(12) United States Patent
Morimoto et al.

(10) Patent No.: US 11,369,776 B2
(45) Date of Patent: Jun. 28, 2022

(54) BALLOON CATHETER AND MANUFACTURING METHOD THEREOF, AND TREATMENT METHOD

(71) Applicant: TERUMO KABUSHIKI KAISHA, Tokyo (JP)

(72) Inventors: Katsumi Morimoto, Kanagawa (JP); Yasuo Kurosaki, Kanagawa (JP); Katsunori Ebata, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 810 days.

(21) Appl. No.: 15/467,002

(22) Filed: Mar. 23, 2017

(65) Prior Publication Data

US 2017/0274185 A1  Sep. 28, 2017

(30) Foreign Application Priority Data

Mar. 23, 2016  (JP) .............................. JP2016-058042

(51) Int. Cl.
*A61M 25/10* (2013.01)
*B05D 1/42* (2006.01)
(Continued)

(52) U.S. Cl.
CPC .............. *A61M 25/10* (2013.01); *A61L 29/08* (2013.01); *A61L 29/16* (2013.01);
(Continued)

(58) Field of Classification Search
CPC .......... A61M 25/10; A61M 2025/1086; A61M 2025/1081; A61M 2025/105;
(Continued)

(56) References Cited

U.S. PATENT DOCUMENTS 9,061,127 B2  6/2015  Weber et al.
9,168,362 B2  10/2015  Morero et al.
(Continued)

FOREIGN PATENT DOCUMENTS

EP  2 271 379 B1  11/2015
EP  2 944 331 A1  11/2015
(Continued)

OTHER PUBLICATIONS

U.S. Appl. No. 15/467,304, filed Mar. 23, 2017, ** Kurosaki et al.
(Continued)

*Primary Examiner* — Brandy S Lee
(74) *Attorney, Agent, or Firm* — Buchanan Ingersoll & Rooney PC (57) ABSTRACT

A balloon catheter that includes an elongated main body extending in an axial direction and a balloon connected to the distal portion of the elongated main body. The balloon includes an interior and is inflatable and deflatable. The balloon catheter also includes a plurality of elongate bodies extending radially away from the outer surface of the balloon. The elongate bodies are crystals of a water-insoluble drug. The elongate bodies each possess an independent longitudinal axis. Each of the elongate bodies includes a base portion at the proximal end of the elongate body. A plurality of elongate body proximal portions extend radially inwardly from the base portion of each of the elongate bodies toward the interior of the balloon. The elongate body proximal portions are continuous extensions of the crystal of the water-insoluble drug.

19 Claims, 6 Drawing Sheets

(51) Int. Cl.
*C30B 29/58* (2006.01)
*C30B 29/62* (2006.01)
*C30B 7/06* (2006.01)
*B05D 1/00* (2006.01)
*A61L 29/08* (2006.01)
*A61L 29/16* (2006.01)
*B05D 1/26* (2006.01)
*B05D 3/00* (2006.01)

(52) U.S. Cl.
CPC .... *A61M 25/1006* (2013.01); *A61M 25/1029* (2013.01); *A61M 25/10185* (2013.11); *B05D 1/002* (2013.01); *B05D 1/26* (2013.01); *B05D 1/42* (2013.01); *B05D 3/007* (2013.01); *C30B 7/06* (2013.01); *C30B 29/58* (2013.01); *C30B 29/62* (2013.01); *A61L 2300/416* (2013.01); *A61L 2300/63* (2013.01); *A61L 2420/02* (2013.01); *A61L 2420/06* (2013.01); *A61M 2025/105* (2013.01); *A61M 2025/1031* (2013.01); *A61M 2025/1081* (2013.01); *A61M 2025/1086* (2013.01); *B05D 2401/20* (2013.01)

(58) Field of Classification Search
CPC .. A61M 2025/1031; A61M 2205/0238; A61M 2025/0057; A61M 25/1029; A61M 2025/1061; A61M 2025/1075; A61L 29/08; A61L 29/16; A61L 2420/06; A61L 2300/416; A61L 2300/63; B05D 1/002; B05D 1/26; B05D 1/42; B05D 2401/20
See application file for complete search history.

(56) References Cited

U.S. PATENT DOCUMENTS

| | | | |
|---|---|---|---|
| 2009/0318848 A1* | 12/2009 | Shippy, III | A61K 31/00 604/20 |
| 2011/0251590 A1* | 10/2011 | Weber | A61L 29/16 604/509 |
| 2014/0271775 A1 | 9/2014 | Cleek et al. | |
| 2014/0358122 A1* | 12/2014 | Yamashita | A61M 25/10 604/509 |
| 2014/0371673 A1* | 12/2014 | Schmitt | A61M 25/1002 604/103.02 |
| 2015/0182732 A1 | 7/2015 | Zeng et al. | |
| 2015/0328441 A1 | 11/2015 | Stroud et al. | |
| 2017/0274186 A1 | 9/2017 | Kurosaki et al. | |
| 2017/0274187 A1 | 9/2017 | Kurosaki et al. | |

FOREIGN PATENT DOCUMENTS

| | | |
|---|---|---|
| EP | 2 944 332 A1 | 11/2016 |
| WO | WO 2014/163091 A1 | 10/2014 |
| WO | WO 2015/181826 A1 | 12/2015 |
| WO | 2017/164278 A1 | 9/2017 |
| WO | WO-2017/164278 A1 | 9/2017 |

OTHER PUBLICATIONS

U.S. Appl. No. 15/467,140, filed Mar. 23, 2017, ** Kurosaki et al.

* cited by examiner

BALLOON CATHETER AND MANUFACTURING METHOD THEREOF, AND TREATMENT METHOD

CROSS-REFERENCES TO RELATED APPLICATIONS

This application claims priority to Japanese Application No. 2016-058042 filed on Mar. 23, 2016 the entire content of which is incorporated herein by reference.

BACKGROUND

The present disclosure generally relates to a balloon catheter provided with a crystalline drug on an outer surface of a balloon, a balloon catheter manufacturing method, and a treatment method using the balloon catheter.

In recent years, balloon catheters have been used for improving lesion affected areas (stenosed parts) in body lumens. A balloon catheter normally includes an elongated shaft portion and a balloon on the distal side of the shaft portion. The balloon is inflatable/deflatable in the radial direction. After the balloon is brought to a target site in the body by way of a thin body lumen while the balloon is in a deflated state, the balloon is inflated, whereby the lesion affected area can be pushed wide open (i.e., widened).

If a lesion affected area is forcibly pushed wide open, however, excessive proliferation of smooth muscle cells may occur, causing new stenosis (restenosis) at the lesion affected area. In view of this possible restenosis problem, drug eluting balloons (DEBs) have recently been used. Drug eluting balloons possess a balloon with an outer surface that is coated with a drug for restraining stenosis. The drug eluting balloon is able to instantaneously release the drug contained in the coating on the outer surface of the balloon to the lesion affected area and deliver the drug to the living body tissue by being inflated, thereby restraining restenosis.

In recent years, it has been becoming clear that the morphological form of the drug in the coating on the balloon surface influences the releasing property of the drug from the balloon surface and/or the tissue transferability of the drug at the lesion affected area. For example, U.S. Patent Application Publication No. 2014/0271775 describes a balloon catheter wherein crystals of a drug are formed in elongate form on a surface of a balloon.

SUMMARY

For enhancing a therapeutic effect, a drug eluting balloon catheter is desirably configured in such a manner that the drug on the surface of the balloon is relatively highly deliverable to living body tissue (i.e., relatively easily transferrable).

The balloon catheter, the balloon catheter manufacturing method and the treatment method using the balloon catheter disclosed here permits a drug to be effectively delivered to living body tissue.

In one aspect of the present disclosure, there is provided a balloon catheter provided on an outer surface of a balloon with a plurality of elongate bodies. The elongate bodies are crystals of a water-insoluble drug extending while having independent long axes. The balloon catheter includes: a plurality of elongate body proximal portions extending from a base portion of each of the elongate bodies toward the inside of the balloon. The elongate body proximal portions are the crystal of the water-insoluble drug continuing from the elongate body.

In the balloon catheter configured as described above, the elongate body proximal portions (which are the crystals continuing from the elongate body) extend into the interior of the balloon. Therefore, the elongate bodies are less liable to fall off (i.e., be removed from) the outer surface of the balloon during delivery to an affected area, so that the drug can be effectively delivered to living body tissue.

The elongate bodies may be hollow at least on a distal side of each of the elongate bodies. The surface areas of the crystals making contact with the living body tissue are thus enlarged. Therefore, the releasing property of the drug from the outer surface of the balloon (i.e., the ability of the drug to be released from the outer surface) and the tissue transferability of the drug (i.e., the transferability of the drug onto the tissue) can be enhanced. The drug can thus be effectively delivered to the living body tissue.

The elongate bodies may each possess a polygonal cross-section orthogonal to a long axis (i.e., longitudinal axis) of each of the elongate bodies. The surface areas of the crystals making contact with the living body tissue are thus enlarged. Therefore, the releasing property of the drug from the outer surface of the balloon and the tissue transferability of the drug can be enhanced, and the drug can be effectively delivered to the living body tissue.

Each of the proximal portions of the elongate bodies may have a maximum width in a cross-section orthogonal to the long axis of the elongate body of not more than 5 μm. This ensures that the relatively narrow elongate body proximal portions are able to enter into the interior of the balloon (i.e., protrude inwards towards the interior of the balloon, beyond the outer surface of the balloon), whereby the elongate bodies can be effectively held on to the balloon.

The plurality of elongate bodies may be independent non-aggregated bodies which are not mutually joined. The plurality of elongate bodies may thus be enhanced in dispersibility, and the surface areas of the crystals making contact with the living body tissue are enlarged. Therefore, the releasing property of the drug from the outer surface of the balloon and the tissue transferability of the drug can be enhanced, and the drug can be effectively delivered to the living body tissue.

The water-insoluble drug may be rapamycin, paclitaxel, docetaxel, or everolimus. Restenosis of a stenosed part in a blood vessel can thus be favorably restrained by the elongate bodies of which at least part is located in the interior of the base layer.

In another aspect of the present disclosure there is provided a method of coating a balloon catheter. The method includes: positioning a balloon catheter to apply a coating solution on an outer surface of a balloon of the balloon catheter, the balloon catheter comprising an elongated tubular body which possesses a distal portion, the balloon being attached to the distal portion of the elongated tubular body, the balloon being a thin film that possesses a plurality of spaced apart holes, the holes extending into the outer surface of the balloon and not fully penetrating through the thin film to communicate with the interior of the balloon; applying the coating solution to the outer surface of the balloon of the balloon catheter, the coating solution containing a water-insoluble drug, an organic solvent and water; and volatilizing the organic solvent to cause growth of crystals of the water-insoluble drug that extend from the outer surface of the balloon, the crystals of the water-insoluble drug extending from the outer surface of the balloon forming a plurality of elongate bodies, each of the plurality of elongate bodies possessing a base portion. The volatilizing of the organic solvent causes growth of the crystal of the water-insoluble drug into the holes on the outer surface of the balloon to form a plurality of elongate body proximal portions. The plurality of elongate body proximal portions continuously extend from the base portion of the elongate body toward the interior of the balloon.

In a further aspect of the present disclosure, there is provided a treatment method for delivering a drug to a lesion affected area in a body lumen. The treatment method includes: introducing a balloon catheter into the living body, the balloon catheter comprising an elongated tubular body, a balloon attached to a distal portion of the elongated tubular body, and a plurality of elongate bodies extending radially outward from the outer surface of the balloon catheter, the elongate bodies being crystals of a water-insoluble drug, each of the elongate bodies possessing a base portion, and each of the elongate bodies comprising a plurality of elongate body proximal portions continuously extending from the base portion of the elongate body toward the interior of the balloon; moving the balloon catheter within the living body into the body lumen to position the balloon of the balloon catheter at the lesion affected area; inflating the balloon to press the balloon against living body tissue of the lesion affected area, the inflating of the balloon causing the elongate bodies to contact the living body tissue; releasing at least some of the plurality of elongate bodies from the outer surface of the balloon; and deflating the balloon and withdrawing the balloon out of the body lumen.

DETAILED DESCRIPTION OF THE PREFERRED EMBODIMENT

Set forth below with reference to the accompanying drawings is a detailed description of embodiments of a balloon catheter, a balloon catheter manufacturing method and a treatment method representing examples of the inventive balloon catheter, balloon catheter manufacturing method and treatment method disclosed here. Note that for convenience of explanation, the dimensional ratios in the drawings may be exaggerated and different from the actual ratios.

Figure 1:
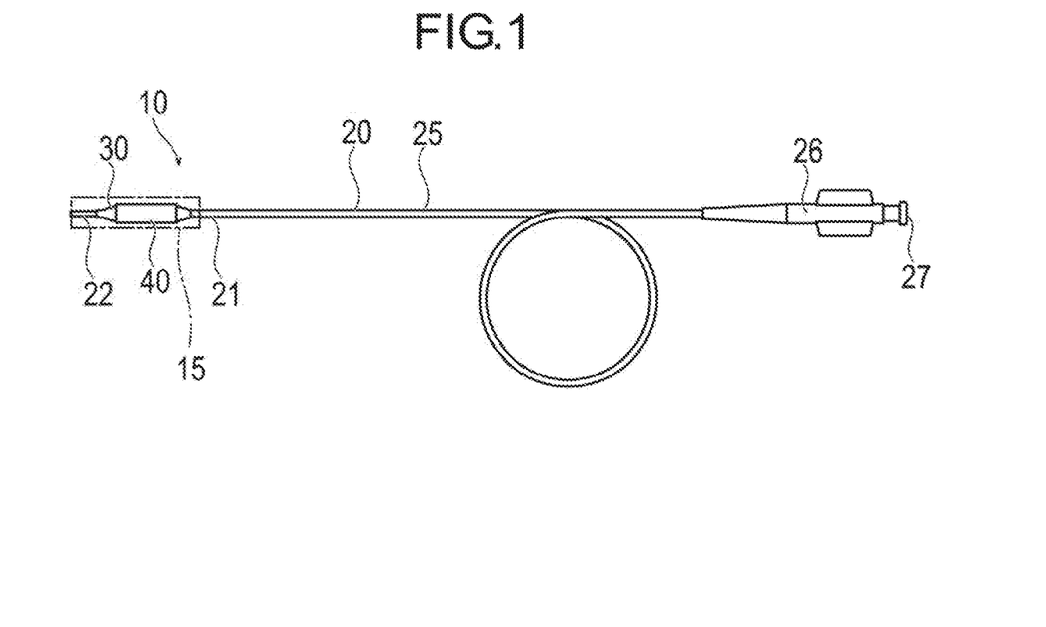
FIG. 1 is a front view of an embodiment of a balloon catheter.
Figure 2:
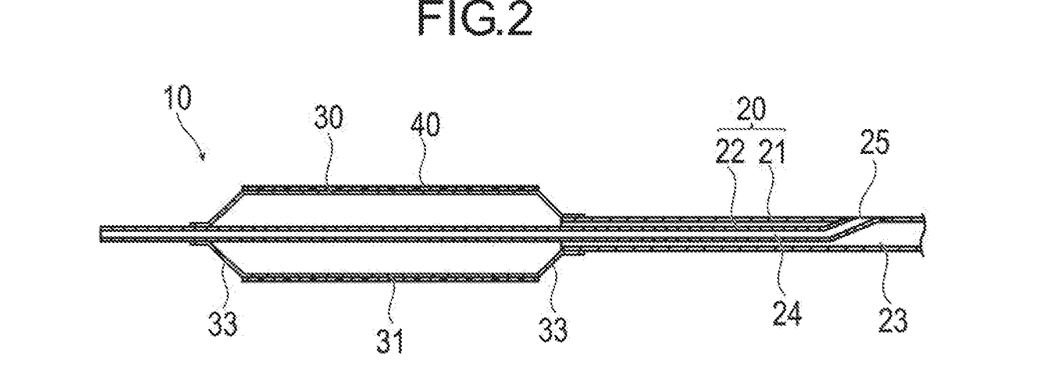
FIG. 2 is a sectional view of a distal portion of the balloon catheter.

As shown in FIGS. 1 and 2, a balloon catheter 10 according to an embodiment of the present disclosure is a drug eluting type catheter with crystals of a drug provided on an outer surface of a balloon 30. Note that in this disclosure the side on which the balloon catheter 10 is inserted into a body lumen will be referred to as "distal end" or "distal side," while the operator's hand side on which the balloon catheter 10 is operated will be referred to as "proximal end" or "proximal side."

First, the structure of the balloon catheter 10 will be described. The balloon catheter 10 includes an elongated catheter main body 20, the balloon 30 provided on a distal portion of the catheter main body 20, a drug-containing coating layer 40 provided on the outer surface of the balloon 30, and a hub 26 attached to a proximal end of the catheter main body 20. The balloon 30 with the coating layer 40 is covered and protected with a protective sheath 15 until put to use (e.g., inflated at the lesion site).

The catheter main body 20 includes an outer tube 21 and an inner tube 22 which is a tube body disposed inside the outer tube 21. The outer tube 21 is a tubular body that is open at the distal and proximal ends. The inner tube 22 is accommodated in a hollow (i.e., an annular space or lumen) inside of the outer tube 21. The distal portion of the catheter main body 20 is a double tube structure. The hollow inside of the inner tube 22 is a guide wire lumen 24 for passing a guide wire therethrough (i.e., a guide wire is positionable in or insertable through the guide wire lumen 24). In the hollow inside of the outer tube 21 and on the outside of the inner tube 22, there is an inflation lumen 23. An inflation fluid for inflating the balloon 30 may pass through the inflation lumen 23. The inner tube 22 is open to the exterior (i.e., surrounding environment) at an opening portion 25. The inner tube 22 protrudes distally beyond the distal end of the outer tube 21.

A proximal-side end portion of the balloon 30 is fixed to the outer surface of the outer tube 21 at a distal portion of the outer tube 21 as illustrated in FIG. 2. A distal-side end portion of the balloon 30 is fixed to the outer surface of the inner tube 21 at a distal portion of the inner tube 22 as illustrated in FIG. 2. This configuration results in the inside of the balloon 30 communicating with the inflation lumen 23. The balloon 30 can thus be inflated by injecting the inflation fluid through the inflation lumen 23 and into the balloon 30. The inflation fluid may be a gas or a liquid. For example, gases such as helium gas, $CO_2$ gas, $O_2$ gas, etc. and liquids such as physiological saline solution, a contrast agent, etc. can be used as the inflation fluid.

At a central portion in the axial direction of the balloon 30, there is a hollow cylindrical straight portion 31 (inflatable portion) having an equal outer diameter when inflated. Tapered portions 33 (where the outer diameter gradually varies) are formed on both sides of the straight portion 31 in the axial direction. The coating layer 40 (which contains a drug) is formed on the whole part of the outer surface of the straight portion 31 (i.e., the entirety of the outer surface of the straight portion 31). The range of the balloon 30 in which the coating layer 40 is applied is not limited to only the straight portion 31. The range of the coating layer 40 application may include at least part of the tapered portions 33 in addition to the straight portion 31, or may include only part of the straight portion 31 (i.e., less than the entirety of the outer surface of the straight portion 31).

The hub 26 is formed with a proximal opening portion 27 that communicates with the inflation lumen 23 of the outer tube 21. The proximal opening portion 27 functions as a port through which the inflation fluid flows in and out.

The length in the axial direction of the balloon 30 is not particularly limited, and is preferably 5 to 500 mm, more preferably 10 to 300 mm, and still more preferably 20 to 200 mm.

The outer diameter of the balloon 30 when the balloon 30 is inflated is not particularly limited, and is preferably 1 to 10 mm, and more preferably 2 to 8 mm.

The outer surface of the balloon 30 is smooth and non-porous before the formation of the coating layer 40. The outer surface of the balloon 30 before the formation of the coating layer 40 may also be formed with a plurality of minute holes 35 that do not pierce through the film of the balloon 30. Alternatively, the outer surface of the balloon 30 may have both a range of being smooth and non-porous and a range of having minute holes 35 that do not pierce through the film of the balloon 30 before the formation of the coating layer 40. The diameter of the minute holes 35 is preferably 0.1 to 5 µm, more preferably 0.2 to 3 µm, and still more preferably 0.3 to 1 µm. The depth of the minute holes 35 is preferably 0.1 to 10 µm, more preferably 0.2 to 5 µm, and still more preferably 0.3 to 2 µm.

The balloon 30 preferably has a certain degree of flexibility and a certain degree of hardness such that the drug can be released from the coating layer 40 on the surface of the balloon 30 when the balloon 30 is inflated at a blood vessel or tissue or the like. Specifically, the balloon 30 is formed from metal or resin. It is preferable that at least the outer surface of the balloon 30 that the coating layer 40 is applied to is formed of resin. Examples of the material which can be used for forming at least the outer surface of the balloon 30 include thermoplastic resins such as polyolefins (e.g., polyethylene, polypropylene, polybutene, ethylene-propylene copolymers, ethylene-vinyl acetate copolymers, ionomers, or mixtures of two or more, of them), flexible polyvinyl chloride resin, polyamides, polyamide elastomers, nylon elastomers polyester, polyester elastomers, polyurethane fluororesins, etc., silicone rubbers, and latex rubbers. Among these, are the polyamides are preferable. Specifically, at least part of the outer surface of an inflated part of the medical device to be coated with the drug is preferably made of a polyamide. The polyamide is not particularly limited so long as the polyamide is a polymer which has an amide linkage. Examples of the polyamide include homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12), etc., copolymers such as caprolactam/lauryllactam copolymer (nylon 6/12), caprolactam/aminoundecanoic acid copolymer (nylon 6/11), caprolactam/ω-aminononanoic acid copolymer (nylon 6/9), caprolactam/hexamethylenediammonium adipate copolymer (nylon 6/66), etc., and aromatic polyamides such as copolymers of adipic acid with metaxylenediamine, or copolymers of hexamethylenediamine with m,p-phthalic acid. Further, polyamide elastomers as block copolymers wherein nylon 6, nylon 66, nylon 11, nylon 12 or the like constitutes hard segments and a polyalkylene glycol, a polyether, an aliphatic polyester or the like constitutes soft segments can also be used as a material of the balloon 30. The above-mentioned polyamides may be used either singly or in combination of two or more the polyamides.

Figure 3:
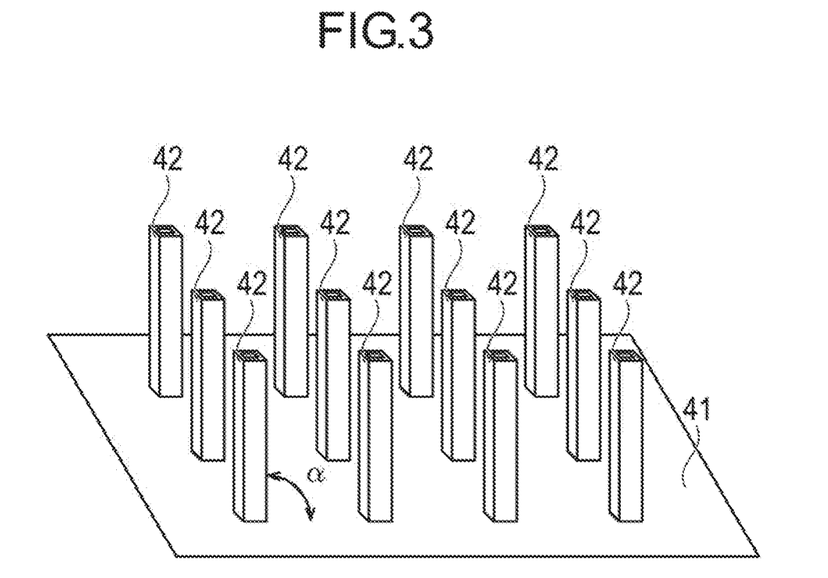
FIG. 3 is a schematic perspective view of elongate bodies consisting of drug crystals on the outer surface of a balloon.
Figure 4:
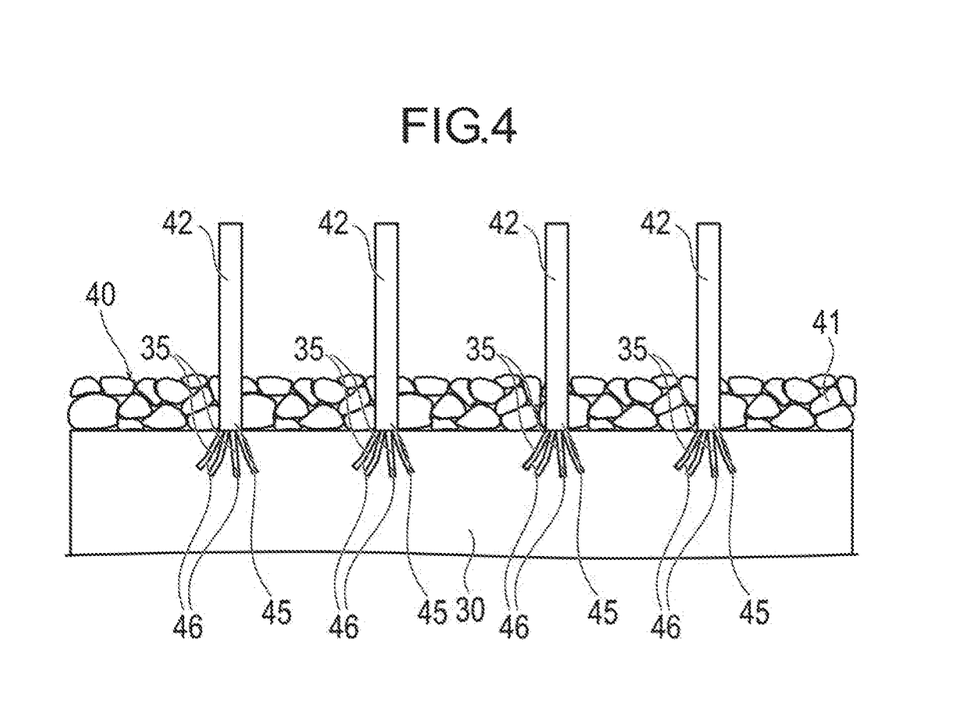
FIG. 4 is a schematic view showing the elongate bodies, consisting of the drug crystals, and a base layer on the outer surface of the balloon.

The coating layer 40 is formed on the outer surface of the balloon 30, either directly or through a pre-treatment layer such as a primer layer between the coating layer 40 and the outer surface of the balloon 30. The method of applying the coating layer 40 on the outer surface of the balloon 30 will be described later. As shown in FIGS. 3 and 4, the coating layer 40 includes a base layer 41 (excipient). The base layer 41 is an additive layer including a water-soluble low-molecular weight compound disposed in a layer form on the outer surface of the balloon 30. The coating layer 40 also includes a plurality of elongate bodies 42 which are crystals of a water-insoluble drug having independent long axes and extending along the long axes (i.e., the elongate bodies 42 each possess longitudinal axis that extends/protrudes towards the surrounding environment from the outer surface of the balloon 30 and/or from the coating layer 40). Each of the elongate bodies 42 may be independently formed from one another (i.e., from the tip of the elongate body 42 to the base of the elongate body 42) and may be spaced apart to not contact any of the adjacent elongate bodies 42 as illustrated in FIG. 3. The long axes (longitudinal axes) of the elongate bodies 42 may be substantially linear (i.e., linearly-shaped) as also shown in FIG. 3. The plurality of elongate bodies 42 may be acicular (needle-shaped). The coating layer 40 also includes a plurality of elongate body proximal portions 46 which extend from a base portion 45 of each of the elongate bodies 42 toward the inside (i.e., interior) of the balloon 30.

The inclination angle α of the elongate bodies 42 relative to the outer surface of the balloon 30 or the base layer 41 is not particularly limited, and the inclination angle α is 45 to 135 degrees, preferably 60 to 120 degrees, more preferably 75 to 105 degrees and still more preferably approximately 90 degrees.

The amount of the drug contained in the coating layer 40 is not particularly limited. The density amount of the drug contained in the coating layer 40 is 0.1 to 10 µg/mm², preferably 0.5 to 5 µg/mm², more preferably 0.5 to 3.5 µg/mm², and still more preferably 1.0 to 3 µg/mm². The amount of the crystals in the coating layer 40 is not particularly limited, and is preferably 5 to 500,000 crystals/(10 µm²), more preferably 50 to 50,000 crystals/(10 µm²), and still more preferably 500 to 5,000 crystals/(10 µm²).

The plurality of elongate bodies 42 wherein crystals have mutually independent long axes are preferably mutually independent non-aggregated bodies. The base portions 45 of the elongate bodies 42 are fixed to the outer surface of the balloon 30. Each of the elongate bodies 42 does not form a composite structure, and is not interlocked, with adjacent elongate bodies 42. The plurality of elongate bodies 42 preferably stand (extend) independently, without making contact with one another (i.e., the elongate bodies 42 preferably extend to be spaced apart from one another). The base portion 45 of the elongate body 42 may be in contact with other base portions 45 of adjacent elongate bodies 42 on the substrate of the balloon 30. In some embodiments, both the plurality of elongate bodies 42 that are non-aggregated bodies and the plurality of elongate bodies 42 that are combined aggregates may be present on the surface of the balloon 30.

The elongate bodies 42 may be hollow (i.e., contain a space in the interior of the elongate body 42) or may be solid but the elongate bodies 42 are preferably hollow. Both hollow elongate bodies 42 and solid elongate bodies 42 may exist on the surface of the balloon 30. At least a portion of the elongate body 42 near the distal end of the elongate body 42 may be hollow. A section of the elongate body 42 in a plane perpendicular (orthogonal) to the long axis of the elongate body 42 has a void (hollow portion). In the elongate body 42 thus having a void, the section of the elongate body 42 in a plane perpendicular (orthogonal) to the long axis is polygonal in shape. The polygon here is, for example, a triangle, a tetragon, a pentagon, or a hexagon. Therefore, the elongate bodies 42 are each formed as an elongate polyhedron with a distal end (or a distal surface) and a proximal end (or a proximal surface) and in which a side surface portion between the distal end (or the distal surface) and the proximal end (or the proximal surface) is composed of a plurality of substantially planar surfaces.

The length in the long axis direction of the elongate bodies 42 having the long axes is preferably 5 to 20 µm, more preferably 9 to 11 µm, and still more preferably around 10 µm. The diameter of the elongate bodies 42 having the long axes is preferably 0.01 to 5 µm, more preferably 0.05 to 4 µm, and still more preferably 0.1 to 3 µm. Examples of the combination of length in the long axis direction and diameter of the elongate bodies 42 having the long axes include a combination of a diameter of 0.01 to 5 µm when the length is 5 to 20 µm, a combination of a diameter of 0.05 to 4 µm when the length is 5 to 20 µm, and a combination of a diameter of 0.1 to 3 µm when the length is 5 to 20 µm. The elongate bodies 42 may be rectilinear in the long axis direction of the elongate bodies 42, and may also be curved in curved line forms (i.e., a curved elongate body 42). Both rectilinear elongate bodies 42 and curved elongate bodies 42 may exist in the coating layer 40 on the outer surface of the balloon 30.

The elongate body proximal portions 46 extend into the interior of the minute holes 35 provided in the outer surface of the balloon 30. The elongate body proximal portions 46 are the crystal of the water-insoluble drug continuing (i.e., continuously extending) from each elongate body 42. More specifically, the elongate body proximal portions 46 extend directly from the base portion 45 (i.e., the proximal-most end surface) of the elongate body 42 toward the interior of the balloon 30 as illustrated in FIG. 4. At least one such elongate body proximal portion 46 is formed, and preferably a plurality of such elongate body proximal portions 46 are formed, to extend from each of the elongate bodies 42. The size of the elongate body proximal portions 46 depends on the size of the holes 35 in the balloon 30. As illustrated in FIG. 4, the plurality of holes 35 may form different angles relative to the outer surface of the balloon 30. The maximum width of the elongate body proximal portions 46 in section orthogonal to the longitudinal axis of the elongate body proximal portions 46 is preferably 0.1 to 5 µm, more preferably 0.2 to 3 µm, and still more preferably 0.3 to 1 µm. The depth of the elongate body proximal portions 46 in the axial direction of each of the elongate body proximal portion 46 (i.e., the depth/extension towards the interior of the balloon 30) is preferably 0.1 to 10 µm, more preferably 0.2 to 5 µm, and still more preferably 0.3 to 2 µm. The axes of the plurality of elongate body proximal portions 46 may form different angles relative to the longitudinal axis of the elongate body 42. When the drug crystals are released from the surface of the balloon 30, each elongate body 42 may be released separately from the plurality of elongate body proximal portions 46, or may be separated and released from the surface of the balloon 30 together with the plurality of elongate body proximal portions 46. Where they are released together, the pluralities of elongate body proximal portions 46 of the adjacent elongate bodies 42 adhered to a blood vessel wall are entangled with one another, whereby appropriate deliverability of the drug is exhibited.

The drug crystals of the crystalline morphological form having the long axes as described above account for at least 50% by volume, and more preferably at least 70% by volume, of the drug crystals on the outer surface of the balloon 30. The elongate bodies 42 (i.e., the crystal particles having the long axes) are formed not to lie flat but to stand (i.e., extend or protrude) in relation to the outer surface of the balloon 30 or the base layer 41. The base layer 41 may exist in a region where the elongate bodies 42 are present, and may not exist in a region where the elongate bodies 42 are absent.

The base layer 41 is present in the state of being distributed into spaces between the plurality of elongate bodies 42 standing together. In other words, spaces between the plurality of elongate bodies 42 may be filled by the base layer 41. In regard of the proportions of the materials constituting the coating layer 40, the crystals of the water-insoluble drug preferably occupy a larger volume than the volume occupied by the base layer 41. The excipient constituting the base layer 41 does not form a matrix. The matrix is a layer which is configured by continuation of a comparatively high-molecular material (e.g., a polymer or the like), which forms a network-like three-dimensional structure, and in which minute spaces are present. The water-insoluble drug constituting the crystals is thus not adhered to the inside of a matrix material. Moreover, the water-insoluble drug constituting the crystals is not embedded in a matrix material.

The base layer 41 is applied in an aqueous solution state to the outer surface of the balloon 30 and dries into a dried base layer 41. The base layer 41 is amorphous. The base layer 41 may be formed of crystal particles. The base layer 41 may exist as a mixture of an amorphous state with crystal particles. The base layer 41 illustrated in FIG. 4 is in a state including crystal particles and/or particulate amorphous portions. The base layer 41 is formed as a layer including the water-insoluble drug. Alternatively, the base layer 41 may be formed as an independent layer that does not include the water-insoluble drug. The thickness of the base layer 41 is 0.1 to 5 µm, preferably 0.3 to 3 µm, and more preferably 0.5 to 2 µm. In addition, the base layer 41 may not be provided.

The layer including the morphological form of the elongate body crystals is low in toxicity and high in stenosis inhibitory effect at the time of delivery into a body. The water-insoluble drug including the hollow elongate body crystalline morphological form has properties promoting penetration into tissue because of a small crystal unit size upon transfer of the drug to the tissue. Since the drug has good solubility, it acts effectively and can inhibit stenosis. In addition, the drug is considered to be less likely to remain in the tissue as large lumps (i.e., in a relatively large lump form) and, therefore, shows low toxicity.

The layer including the elongate body crystalline morphological form has a plurality of substantially uniform elongate bodies 42, and the elongate bodies 42 are substantially uniformly standing (i.e., extending or protruding) together on the surface with which their base portions 45 make contact. The size (the length in the long axis direction) of the crystals transferred to the tissue is thus as small as approximately 10 µm. For this reason, the drug uniformly acts on the lesion affected area, with an enhanced ability to penetrate into the tissue. There is also no possibility that an excess amount of the drug might remain at the affected area for an excess of time because the size of the crystals transferred is relatively small. For this reason, it is considered that the drug can show a high stenosis inhibitory effect, without showing toxicity.

The drug in the coating on the outer surface of the balloon 30 may include an amorphous phase. The crystals and the amorphous phase may be disposed regularly in the coating layer 40. Alternatively, the crystals and the amorphous phase may be disposed irregularly.

The protective sheath 15 is a member for inhibiting the drug from falling off the balloon 30 (i.e., being removed from the surface of the balloon). The protective sheath 15 is removed (e.g., retracted) before the expansion of the balloon 30 of the balloon catheter 10. The protective sheath 15 is formed from a flexible material. Examples of the protective sheath 15 material include thermoplastic resins such as polyolefins (e.g., polyethylene, polypropylene, polybutene, ethylene-propylene copolymers, ethylene-vinyl acetate copolymers, ionomers, or mixtures of two or more of them), flexible polyvinyl chloride resin polyamides, polyimide elastomers, polyesters, polyester elastomers, polyurethane fluororesins, etc., silicone rubbers, and latex rubbers.

Figure 5:
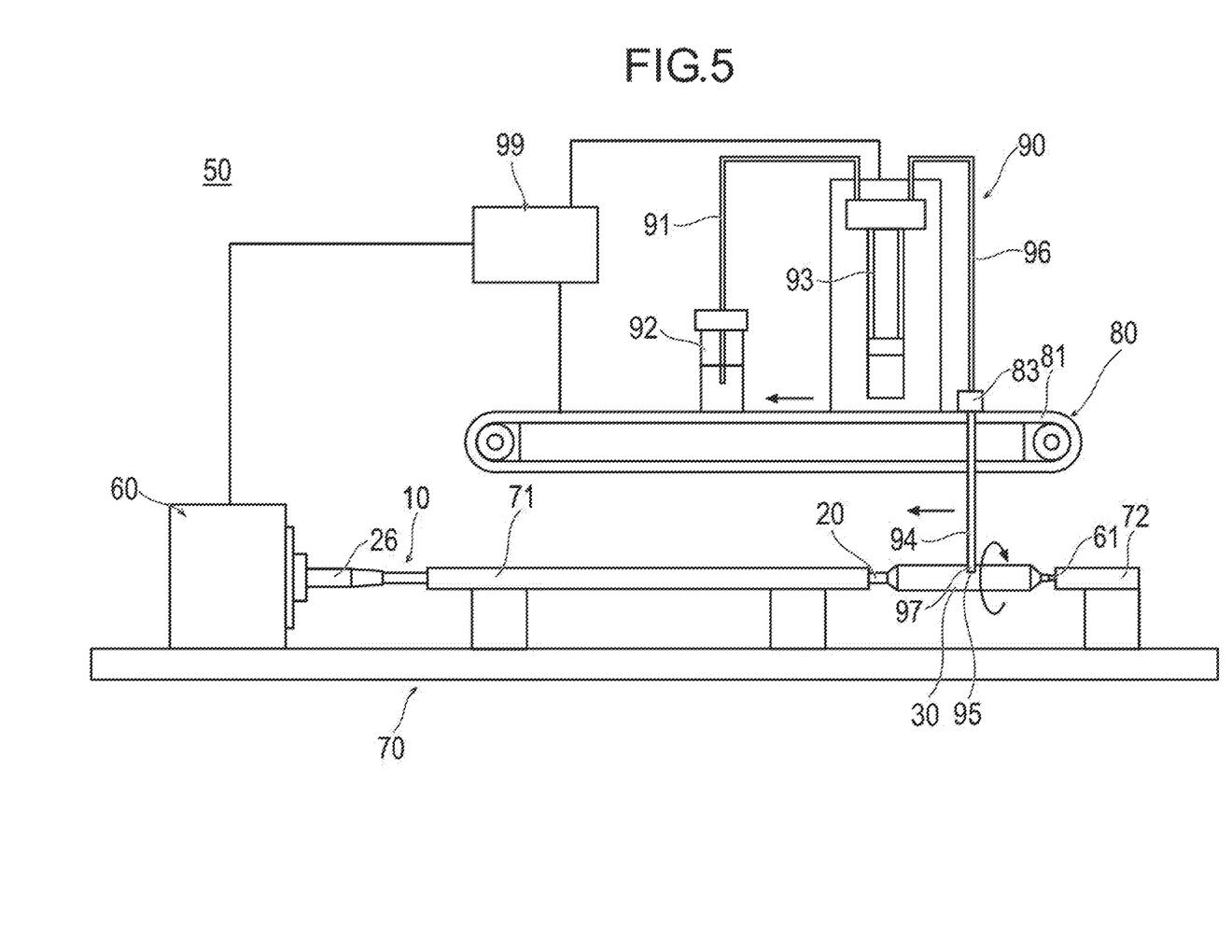
FIG. 5 is a schematic view of a balloon coating apparatus.
Figure 6:
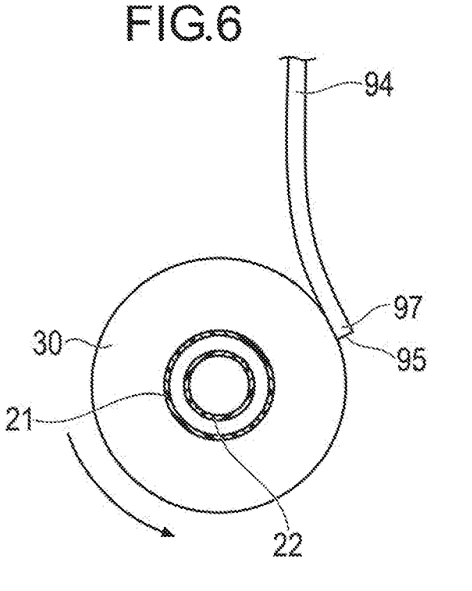
FIG. 6 is a sectional view of a dispensing tube in contact with the balloon.

A balloon coating apparatus 50 for forming the coating layer 40 on the balloon 30 will now be described. As shown in FIGS. 5 and 6, the balloon coating apparatus 50 includes a rotation mechanism section 60 (a rotation mechanism) for rotating the balloon catheter 10 and a support base 70 for supporting the balloon catheter 10. The balloon coating apparatus 50 further includes an application mechanism section 90 that includes a dispensing tube 94 for applying a coating solution to an outer surface of the balloon 30, a movement mechanism section 80 for moving the dispensing tube 94 relative to the balloon 30 (e.g., in the axial direction), and a control unit 99 for controlling the balloon coating apparatus 50.

The rotation mechanism section 60 holds the hub 26 of the balloon catheter 10, and rotates the balloon catheter 10 around an axis of the balloon 30 by a drive source, such as a motor, incorporated in the rotation mechanism section 60. The balloon catheter 10 is held with a core member 61 inserted in the guide wire lumen 24. The core member 61 helps prevent the coating solution from flowing into the guide wire lumen 24. A three-way cock capable of operating the opening/closing of a passage or passages is connected to the proximal opening portion 27 of the hub 26 for allowing a fluid to be introduced into the inflation lumen 23.

The support base 70 includes a tubular proximal-side support section 71 that accommodates the catheter main body 20 in the support section 71 and rotatably supports the catheter main body 20. The support base 70 also includes a distal-side support section 72 that rotatably supports the core member 61. The distal-side support section 72 may, if possible, rotatably support a distal portion of the catheter main body 20, instead of the core member 61.

The movement mechanism section 80 includes a movable base 81 which can be moved rectilinearly in a direction parallel to the axis of the balloon 30 (i.e., in the axial direction) and a tube fixing section 83 to which the dispensing tube 94 is fixed (i.e., held or attached). The movable base 81 can be moved rectilinearly by a drive source, such as a motor, incorporated in the movable base 80. The tube fixing section 83 fixes an upper end of the dispensing tube 94 relative to the movable base 81. The dispensing tube 94 thus moves rectilinearly in a direction parallel to the axis of the balloon 30 (i.e., in the axial direction) when the movable base 81 moves. The application mechanism section 90 is also mounted on the movable base 81, and the movable base 81 moves the application mechanism section 90 rectilinearly in both directions along the axis of the balloon 30 (i.e., proximally and distally along the axial direction of the balloon 30).

The application mechanism section 90 is a section that applies the coating solution to the outer surface of the balloon 30. The application mechanism section 90 includes a container 92 containing the coating solution, a feed pump 93 that feeds the coating solution at an arbitrary feed rate, and the dispensing tube 94 that applies the coating solution to the balloon 30.

The feed pump 93 is, for example, a syringe pump. The feed pump 93 can draw the coating solution from the container 92 through a suction tube 91 and feed the coating solution into the dispensing tube 94 through a supply tube 96 at an arbitrary feed rate based on control applied by the control unit 99. The feed pump 93 is disposed on the movable base 81 and can be moved rectilinearly by the movement of the movable base 81. The feed pump 93 is not limited to being a syringe pump so long as it can feed the coating solution. The feed pump 93 may be, for example, a tube pump.

The dispensing tube 94 is a member which communicates with the supply tube 96 and discharges the coating solution to the outer surface of the balloon 30 supplied from the feed pump 93 through the supply tube 96. The dispensing tube 94 is a flexible circular pipe-shaped member (i.e., a tubular member). The upper end of the dispensing tube 94 is fixed to the tube fixing section 83 and extends downward in the vertical direction from the tube fixing section 83. The dispensing tube 94 includes an opening portion 95 (i.e., an opening) at a discharge end 97. The discharge end is the lower end in the vertical direction as illustrated in FIG. 5. The dispensing tube 94 can be moved by the movable base 81 rectilinearly in both directions along the axial direction of the balloon catheter 10 (i.e., proximally and distally in the axial direction of the balloon catheter 10) together with the feed pump 93 disposed on the movable base 81. The dispensing tube 94 can supply the coating solution to the outer surface of the balloon 30 while the dispensing tube 94 is bent by being pressed against the balloon 30.

The dispensing tube 94 may not necessarily possess a circular pipe-shape as long as the dispensing tube 94 can supply the coating solution. The dispensing tube 94 may additionally not necessarily extend in the vertical direction as long as the dispensing tube 94 can discharge the coating solution through the opening portion 95.

The dispensing tube 94 is preferably formed from a flexible material such that a contact burden (force) on the balloon 30 is reduced and variations in the contact position attendant on the rotation of the balloon 30 can be absorbed by flexure of the dispensing tube 94. Examples of the dispensing tube 94 material include polyolefins such as polyethylene polypropylene, etc., cyclic polyolefins, polyesters, polyamides, polyurethane, and fluororesins such as PTFE (polytetrafluoroethylene), ETFE (tetrafluoroethylene-ethylene copolymer), PFA (tetrafluoroethylene-perfluoroalkyl vinyl ether copolymer), FEP (tetrafluoroethylene-hexafluoropropylene copolymer), etc., but the material is not particularly limited as long as the material is flexible and deformable.

The outer diameter of the dispensing tube 94 is not particularly limited. For example, the outer diameter of the dispensing tube 94 may be 0.1 to 5.0 mm, preferably 0.15 to 3.0 mm, and more preferably 0.3 to 2.5 mm. The inner diameter of the dispensing tube 94 is also not particularly limited, is the inner diameter of the dispensing tube 94 may be, for example, 0.05 to 3.0 mm, preferably 0.1 to 2.0 mm, and more preferably 0.15 to 1.5 mm. The length of the dispensing tube 94 is not particularly limited and is preferably a length of not more than 5 times the balloon diameter. For example, the dispensing tube 94 length may be 1.0 to 50 mm, preferably 3 to 40 mm, and more preferably 5 to 35 mm.

The control unit 99 is composed for example, of a computer, and unifyingly controls the rotation mechanism section 60, the movement mechanism section 80, and the application mechanism section 90. The control unit 99 can thus unifyingly control the rotating speed of the balloon 30, the moving speed of the dispensing tube 94 in the axial direction of the balloon 30, the drug discharge rate from the dispensing tube 94, and so on.

The coating solution supplied from the dispensing tube 94 to the balloon 30 is a solution or suspension containing the constituent materials of the coating layer 40. The coating solution supplied from the dispensing tube 94 contains a water-insoluble drug, an excipient, an organic solvent, and water. After the coating solution is supplied to the outer surface of the balloon 30, the organic solvent and water volatilize, whereby a coating layer 40 including a plurality of elongate bodies 42 is formed on the outer surface of the balloon 30. The plurality of elongate bodies 42 formed in this manner are crystals of the water-insoluble drug extending while having independent longitudinal axes.

The viscosity of the coating solution is 0.5 to 1,500 cP, preferably 1.0 to 500 cP, and more preferably 1.5 to 100 cP.

The water-insoluble drug means a drug which is insoluble or difficultly soluble in water. Specifically the water-insoluble drug is a drug possessing solubility in water of less than 5 mg/mL at pH 5 to 8. The solubility may be less than 1 mg/mL, or, further, may be less than 0.1 mg/mL. The water-insoluble drug includes fat-soluble drugs.

Some preferred examples of the water-insoluble drug include immunosuppressants, e.g., cyclosporines inclusive of cyclosporine, immunoadjuvants such as rapamycin, carcinostatics such as paclitaxel, antiviral or antibacterial agents, antineoplastic agents, analgesic and anti-inflammatory agents, antibiotics, antiepileptics, anxiolytic agents, antiparalytic agents, antagonists, neuron blocking agents, anticholinergic and cholinergic agents, muscarine antagonists and muscarine agents, antiadrenergic agents, antiarrhythmic agents, antihypertensive agents, hormone preparations, and nutritional supplements.

The water-insoluble drug is preferably at least one selected from a group composed of rapamycin, paclitaxel, docetaxel, and everolimus. The rapamycin, paclitaxel, docetaxel, and everolimus that may be used for the water-insoluble drug include their analogs and/or derivatives as long as the analogs and/or derivatives have equivalent drug activity to the original. For example, paclitaxel and docetaxel are in an analog relation. Rapamycin and everolimus are in a derivative relation. Among these, paclitaxel is preferable.

The excipient constitutes the base layer 41 on the balloon 30. The excipient includes a water-soluble low-molecular weight compound. The molecular weight of the water-soluble low-molecular weight compound is 50 to 2,000, preferably 50 to 1,000, more preferably 50 to 500, and still more preferably 50 to 200. The amount of the water-soluble low-molecular weight compound is preferably 5 to 10,000 parts by weight, more preferably 5 to 200 parts by weight, and still more preferably 8 to 150 parts by weight, per 100 parts by weight of the water-insoluble drug. Examples of the applicable constituent material of the water-soluble low-molecular weight compound include serine ethyl esters, citric acid esters, polysorbates, water-soluble polymers, sugars, contrast agents, amino acid esters, glycerol esters of short-chain monocarboxylic acids, pharmaceutically acceptable salts and surfactants, and mixtures of two or more of these. The water-soluble low-molecular weight compound is characterized in that the water-soluble low-molecular weight compound has a hydrophilic group and a hydrophobic group and is soluble in water. The water-soluble low-molecular weight compound preferably is non-swellable or difficultly swellable. The excipient is preferably amorphous on the balloon 30. The excipient including the water-soluble low-molecular weight compound has an effect of uniformly dispersing the water-insoluble drug on the surface of the balloon 30. The excipient constituting the base layer 41 is preferably not a hydrogel. The base layer 41 is rapidly dissolved without being swelled upon contact with an aqueous solution because the base layer 41 is a low-molecular weight compound. The crystal particles of the water-insoluble drug on the surface of the balloon 30 becomes easily releasable because the base layer 41 becomes easily soluble upon inflation of the balloon 30 in a blood vessel. The base layer 41 thus increases the amount of the drug crystal particles adhered to the blood vessel. When the base layer 41 is a matrix composed of a contrast agent such as Ultravist (registered trademark), the crystal particles are embedded in the matrix, and crystals are not produced to extend from the substrate of the balloon 30 toward the outside of the matrix. On the other hand, the elongate bodies 42 according to the present embodiment extend from the surface of the substrate of the balloon 30 to the outside of the base layer 41. The length of that portion of the elongate body 42 which is located on the outside of the base layer 41 is greater than the length of that portion of the elongate body 42 which is located inside the base layer 41 (i.e., the portion of the elongate body 42 that protrudes beyond the outer surface, of the base layer 41 is longer than the portion of the elongate body 42 that is embedded within the base layer 41). The base layer 41 is formed to support the base portions 45 of the elongate bodies 42 which are crystals.

The organic solvent is not particularly limited. Examples of the organic solvent include tetrahydrofuran acetone, glycerin, ethanol, methanol, dichloromethane, hexane, and ethyl acetate. Among these, mixed solvents of some of tetrahydrofuran, ethanol, and acetone are preferable.

Examples of a mixture of an organic solvent with water include a mixture of tetrahydrofuran and water, a mixture of tetrahydrofuran and ethanol and water, a mixture of tetrahydrofuran and acetone and water, a mixture of acetone and ethanol and water, and a mixture of tetrahydrofuran and acetone and ethanol and water.

A method of forming crystals of the water-insoluble drug on the outer surface of the balloon 30 by use of the balloon coating apparatus 50 will be described below.

First, the inflation fluid is supplied into the balloon 30 through the three-way cock connected to the proximal opening portion 27 of the balloon catheter 10 to inflate the balloon 30. Next, the three-way cock is operated to seal up the inflation lumen 23 while the balloon 30 is inflated, thereby maintaining the balloon 30 in the inflated state. The balloon 30 is inflated with a pressure (e.g., 4 atm) lower than a pressure (e.g., 8 atm) at the time of use in a blood vessel in a living body. The coating layer 40 can also be formed on the outer surface of the balloon 30 without inflating the balloon 30. In that case, it is unnecessary to supply the inflation fluid into the balloon 30.

Subsequently, the balloon catheter 10 is rotatably disposed on the support base 70, and the hub 26 is connected to the rotation mechanism section 60 while the dispensing tube 94 is positioned to not contact the outer surface of the balloon 30.

The position of the movable base 81 is next adjusted to position the dispensing tube 94 relative to the balloon 30. The dispending tube 94 is first positioned on the most distal side in a surface region of the balloon 30 where the coating layer 40 is to be formed. As an example, the extending direction (discharge direction) of the dispensing tube 94 is opposite to the rotating direction of the balloon 30. Therefore, at the position where the dispensing tube 94 is put in contact with the balloon 30, the balloon 30 is rotated in the direction opposite to the discharge direction in which the coating solution is discharged from the dispensing tube 94. This rotation opposite to the discharge direction gives a physical stimulus to the coating solution, whereby formation of crystal nuclei of the drug crystal can be promoted. The crystals of the water-insoluble drug formed on the outer surface of the balloon 30 are liable to be formed assuming a morphological form wherein the crystals include a plurality of elongate bodies 42 having mutually independent long axes because the extending direction (discharge direction) of the dispensing tube 94 toward the opening portion 95 is opposite to the rotating direction of the balloon 30. The extending direction of the dispensing tube 94 may not necessarily be opposite to the rotating direction of the balloon 30. The extending direction of the dispensing tube 94 may be the same as or perpendicular to the rotating direction.

The coating solution is then supplied to the dispensing tube 94 while adjusting the feed rate by the feed pump 93, the balloon catheter 10 is rotated by the rotation mechanism section 60, and the movable base 81 is moved so that the dispensing tube 94 is gradually moved proximally along the axial direction of the balloon 30. The coating solution discharged from the opening portion 95 of the dispensing tube 94 is applied to the outer surface of the balloon 30 to apply the coating solution in a spiral shape, since the dispensing tube 94 is moved relative to the balloon 30 in the axial direction of the balloon 30.

The moving speed of the dispensing tube 94 is not particularly limited, and is, for example, 0.01 to 2 mm/second, preferably 0.03 to 1.5 mm/second, and more preferably 0.05 to 1.0 mm/second. The discharge rate of the coating solution from the dispensing tube 94 is not particularly limited, and is, for example, 0.01 to 1.5 µL/second, preferably 0.01 to 1.0 µL/second, and more preferably 0.03 to 0.8 µL/second. The rotation speed of the balloon 30 is not particularly limited, and is, for example, 10 to 300 rpm, preferably 30 to 250 rpm, and more preferably 50 to 200 rpm. The diameter of the balloon 30 when the balloon 30 is coated with the coating solution is not particularly limited, and is, for example, 1 to 10 mm, and preferably 2 to 7 mm.

Thereafter, the organic solvent contained in the coating solution applied to the surface of the balloon 30 volatilizes earlier than water. The organic solvent thus volatilizes in a condition where the water-insoluble drug, the water-soluble low-molecular weight compound and water are left on (retained on) the surface of the balloon 30. When the organic solvent thus volatilizes with water left in the coating, the water-insoluble drug is precipitated inside the water-soluble low-molecular weight compound that contains water, and crystals gradually grow from crystal nuclei. This induces the drug crystals of a morphological form wherein the crystals include a plurality of elongate bodies 42 having mutually independent long axes and the elongate body proximal portions 46 to form on the outer surface of the balloon 30. After the organic solvent has volatilized and the drug crystals are precipitated into the plurality of elongate bodies 42 and the elongate body proximal portions 46, water evaporates more slowly than the organic solvent, and the base layer 41 including the water-soluble low-molecular weight compound is formed. The time taken for evaporation of water is appropriately set in accordance with the kind of the drug, the kind of the water-soluble low-molecular weight compound, the kind of the organic solvent, the ratios of the amounts of the materials, the coating amount of the coating solution, and the like. The time for the evaporation of water is, for example, approximately 1 to 600 seconds.

The dispensing tube 94 is then gradually moved in the axial direction of the balloon 30 while the balloon 30 is rotated by the rotation mechanism section 60, whereby the coating layer 40 is gradually formed on the outer surface of the balloon 30 along the axial direction of the balloon 30. After the coating layer 40 including the elongate bodies 42 is formed over the whole range of coating for the balloon 30, the rotation mechanism section 60, the movement mechanism section 80, and the application mechanism section 90 operations are stopped.

The balloon catheter 10 is then removed from the balloon coating apparatus 50, which completes the coating of the balloon 30. Thereafter, the inflation fluid is discharged from the balloon 30, whereby the balloon 30 is deflated and folded. Next, the balloon 30 is covered with the tubular protective sheath 15 (see FIG. 1) to complete the manufacture of the balloon catheter 10. The protective sheath 15 is a member for inhibiting the drug from falling off (i.e., being scraped off or removed from) the balloon 30. The protective sheath 15 is removed (e.g. retracted) before of the expansion of the balloon 30 of the balloon catheter 10.

A method of using the balloon catheter 10 according to an embodiment of the disclosure wilt be described below. The method will be described in relation to an example case of treating a stenosed part in a blood vessel in a living body.

First, the operator percutaneously punctures a blood vessel and places an introducer (not shown) indwelling by a known method such as Seldinger method. Next, the protective sheath 15 is removed from the balloon catheter 10, priming is performed and a guide wire 200 (see FIG. 7) is inserted into the guide wire lumen 24. In this state, the guide wire 200 and the balloon catheter 10 are inserted into the blood vessel through the inside of the introducer. The balloon-catheter 10 is subsequently moved forward along the guide wire 200 end the balloon 30 is delivered to a stenosed part 300 in the living body. A guiding catheter may instead be used for delivering the balloon catheter 10 to the stenosed part 300.

Figure 7:
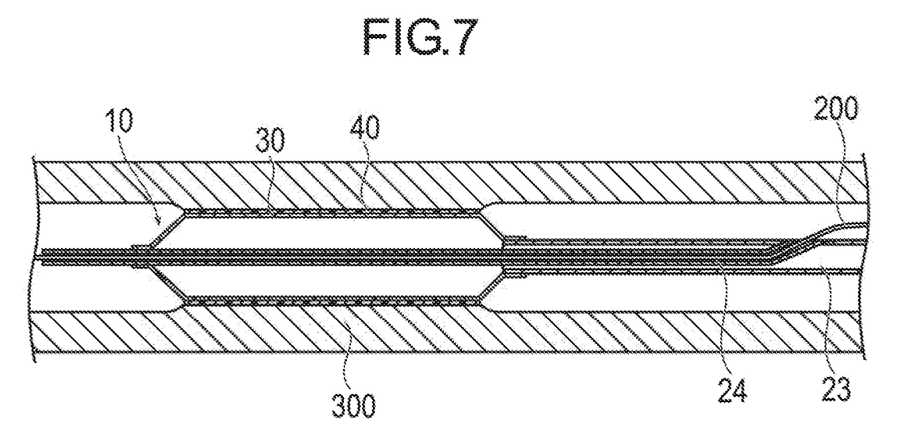
FIG. 7 is a sectional view showing the stenosed part of a blood vessel being pushed wide open by the balloon catheter.

A predetermined quantity of an inflation fluid is subsequently injected into the proximal opening portion 27 of the hub 26 by use of an indeflator or syringe or the like, and the inflation fluid is fed through the inflation lumen 23 into the balloon 30. As shown in FIG. 7, the folded balloon 30 is inflated by injecting the inflation fluid, and the stenosed part 300 is pushed wide open by the balloon 30 (i.e., the balloon 30 expands to and applies a force to expand/widen the stenosed part 300). The coating layer 40 containing the drug crystals provided on the outer surface of the balloon 30 thus makes contact with the stenosed part 300. As shown in FIG. 4, the elongate body proximal portions 46 (which are the crystal continuing from each of the elongate bodies 42) contained in the coating layer 40 extend into the inside (i.e., inwards beyond the outer surface) of the balloon 30. Therefore, the elongate bodies 42 are less likely to fail off (e.g., be removed from) the outer surface of the balloon 30 during delivery to the stenosed part 300, so that the drug can be effectively delivered to the living body tissue. Consequently, restenosis of the stenosed part 300 is effectively restrained.

When the balloon 30 is inflated and the coating layer 40 is thereby pressed against living body tissue, the base layer 41 composed of the water-soluble low-molecular weight compound contained in the coating layer 40 is dissolved relatively slowly or relatively rapidly. During the dissolution, the drug is delivered to the living body tissue. The inflation of the balloon 30 additionally causes cracking of the base layer 41, which facilitates the dissolution of the base layer 41. This cracking helps enable the elongate bodies 42 as the drug crystals to be easily released from the base layer 41. Accordingly, the deliverability of the drug can be arbitrarily set by controlling the material and thickness of the base layer 41, and the like.

The inflation fluid is then discharged by drawing the inflation fluid out via the proximal opening portion 27 of the hub 26, whereby the balloon 30 is deflated and put into a folded state. The guide wire 200 and the balloon catheter 10 are next withdrawn out of the blood vessel through the introducer, to complete the procedure.

As has been described above, the balloon catheter 10 according to this embodiment includes a plurality of elongate bodies 42 on the outer surface of the balloon 30. The plurality of elongate bodies 42 are the crystals of the water-insoluble drug extending while having independent long axes. The balloon catheter 10 includes a plurality of elongate body proximal portions 46 extending from the base portion of each of the elongate bodies 42 toward the interior of the balloon 30. The elongate body proximal portions 48 are the crystal of the water-insoluble drug continuing from the elongate body 42. The balloon catheter 10 is configured in this way with the elongate body proximal portions 46 (which are the crystal continuing from each of the elongate bodies 42) extending into the inside of the balloon 30, so that the elongate bodies 42 are less liable (likely) to fall off the balloon 30 during delivery to the stenosed part 300. This configuration of the balloon catheter 10 thus allows the drug to be effectively delivered to the living body tissue.

The elongate bodies 42 may be hollow at least on the distal side of the elongate bodies. The surface areas of the crystals making contact with the living body tissue are thus enlarged. Therefore, the releasing property of the drug from the outer surface of the balloon 30 and the tissue transferability of the drug can be enhanced and the drug can be effectively delivered to the living body tissue.

The elongate bodies 42 may also each be polygonal in a cross-section orthogonal to the long axis of each of the elongate bodies 42. The surface areas of the crystals making contact with the living body tissue are thus enlarged. The releasing property of the drug from the outer surface of the balloon 30 and the tissue transferability of the drug can thereby be enhanced, and the drug can be effectively delivered to the living body tissue.

The elongate body proximal portions 46 may each have a maximum width in section orthogonal to the longitudinal axis of the elongate body 42 of not more than 5 μm. This helps ensure that the relatively narrow elongate body proximal portions 46 enter into the inside of the balloon 30, whereby, the elongate bodies 42 can be effectively held on to the balloon 30.

The plurality of elongate bodies 42 may be independent non-aggregated bodies which are not mutually joined. The plurality of elongate bodies 42 may thus be enhanced in dispersibility, and the surface areas of the crystals making contact with the living body tissue are enlarged. Therefore, the releasing property of the drug from the outer surface of the balloon 30 and the tissue transferability of the drug can be enhanced, and the drug can be effectively delivered to the living body tissue.

The water-insoluble drug may be rapamycin, paclitaxel, docetaxel, or everolimus. Restenosis of a stenosed part in a blood vessel can thus be favorably restrained by the elongate bodies 42.

The method of manufacturing the balloon catheter 10 according to the present embodiment is a method of manufacturing the balloon catheter 10 provided on the outer surface of the balloon 30 with the plurality of elongate bodies 42 which are crystals of the water-insoluble drug extending while having independent long axes. The manufacturing method includes: the step of supplying the coating solution containing the drug, an organic solvent and water to the outer surface of the balloon 30, the outer surface provided with the plurality of holes 35 having a maximum width of not more than 5 μm; and the step of volatilizing the organic solvent to cause growth of crystals of the water-insoluble drug from the outer surface of the balloon 30, thereby forming the plurality of elongate bodies 42, and to cause growth of the crystal of the water-insoluble drug in the inside of the holes 35 in the state of continuing from the base portion 45 of the elongate body 42, thereby forming the plurality of elongate body proximal portions 46. According to the method of manufacturing the balloon catheter 10, the coating solution is supplied to the outer surface of the balloon 30 that is formed with the plurality of holes 35 having a maximum width of not more than 5 μm. Therefore, crystal growth occurs in/into the inside of the holes 35, whereby the plurality of elongate body proximal portions 46 extending from the base portion 45 of each of the elongate bodies 42 toward the inside of the balloon 30 can be formed.

The present disclosure involves the treatment (therapeutic) method for delivering a drug to a lesion affected area in a body lumen by use of the balloon catheter 10. The treatment method includes: the step of inserting the balloon 30 into the body lumen to deliver the balloon 30 to the lesion affected area; the step of inflating the balloon 30 to bring the elongate bodies 42 into contact with living body tissue; and the step of deflating the balloon 30 and withdrawing the balloon 30 out of the body lumen. In the treatment method configured as above, use is made of the balloon 30 wherein the elongate body proximal portions 46 which are the crystal continuing from the elongate body 42 extend into the inside of the balloon 30. Therefore, the elongate bodies 42 are less liable to fall off the balloon 30 during delivery to the stenosed part 300, so that the drug can be effectively delivered to the living body tissue.

The present disclosure is not limited to the embodiment discussed above, and various modifications can be made by those skilled in the art within the technical thought of the present disclosure. For example, although the balloon catheter 10 according to the above embodiment is of the rapid exchange type, the balloon catheter may instead be of the over-the-wire type.

The method for supplying the coating solution to the balloon 30 is additionally not limited to using the dispensing tube 94. For example, there may be used a dipping method wherein a container is filled with the coating solution, and the balloon 30 is immersed in the coating liquid and pulled up whereby the coating liquid is applied to the outer surface of the balloon 30. Alternatively, a method of spraying a solution onto the balloon may be used.

Figure 8:
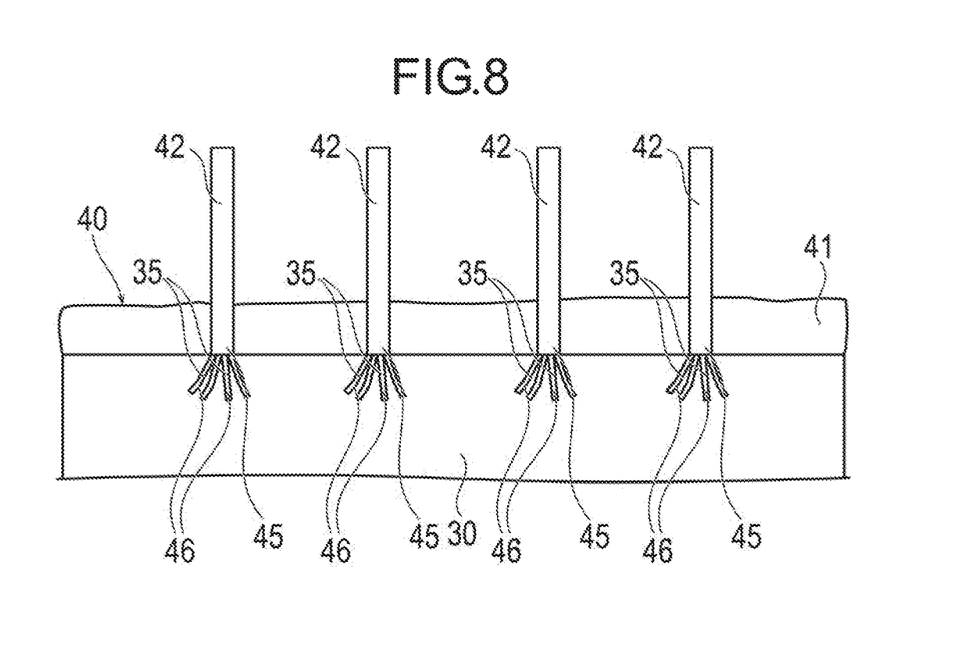
FIG. 8 is a schematic view showing elongate bodies and a base layer in the case where the base layer is in a film-formed amorphous state.

The base layer 41 exists as an amorphous phase, crystal particles, or a mixture thereof. While the base layer 41 shown in FIG. 4 includes crystal particles and/or particulate amorphous portions, the base layer 41 may be in a film-formed amorphous state as depicted in FIG. 8.

Figure 9:
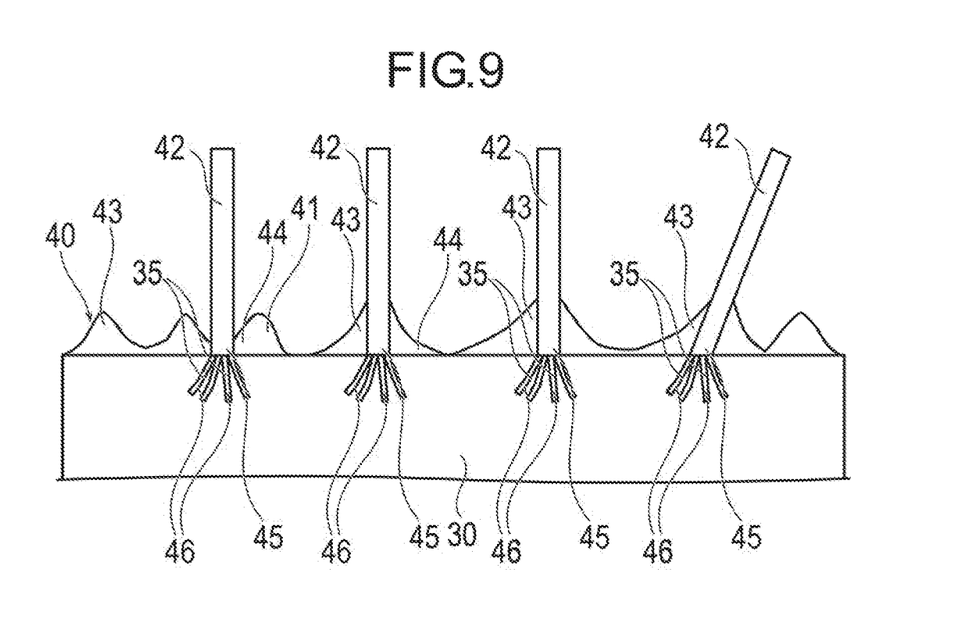
FIG. 9 is a schematic view showing elongate bodies and a base layer on an outer surface of a balloon.

In addition, the base layer 41 may be an additive layer possessing a rugged pattern (recesses and projections) as shown in FIG. 9. The height of the rugged pattern is 0.1 to 5 μm. The elongate bodies 42 as crystals project from projected portions 43 constituting the rugged pattern of the base layer 41. In other words, the projected portions 43 of the base layer 41 support the elongate bodies 42 as the crystals. The base layer 41 may include projected portions 43 from which the elongate bodies 42 do not project. The elongate bodies 42 as the crystals may project from recessed portions 44 constituting the rugged pattern of the base layer 41. The base layer 41 may include both projected portions 43 that support the elongate bodies 42 and projected portions 43 that do not support the elongate bodies 42. The base layer 41 may include both the recessed portions 44 that support the elongate bodies 42 and the recessed portions 44 that do not support the elongate bodies 42. The base layer 41 may also include both the projected portions 43 that support the elongate bodies 42 and the recessed portions 44 that support the elongate bodies 42. The elongate bodies 42 may project obliquely from the base layer 41 such as to be inclined relative to the outer surface of the balloon 30 (e.g., as illustrated by one of the elongate bodies 42 shown in FIG. 9). The base layer 41 may have both the elongate bodies 42 that are substantially perpendicular to the outer surface of the balloon 30 and the elongate bodies 42 that are inclined relative to the outer surface of the balloon 30.

Figure 10:
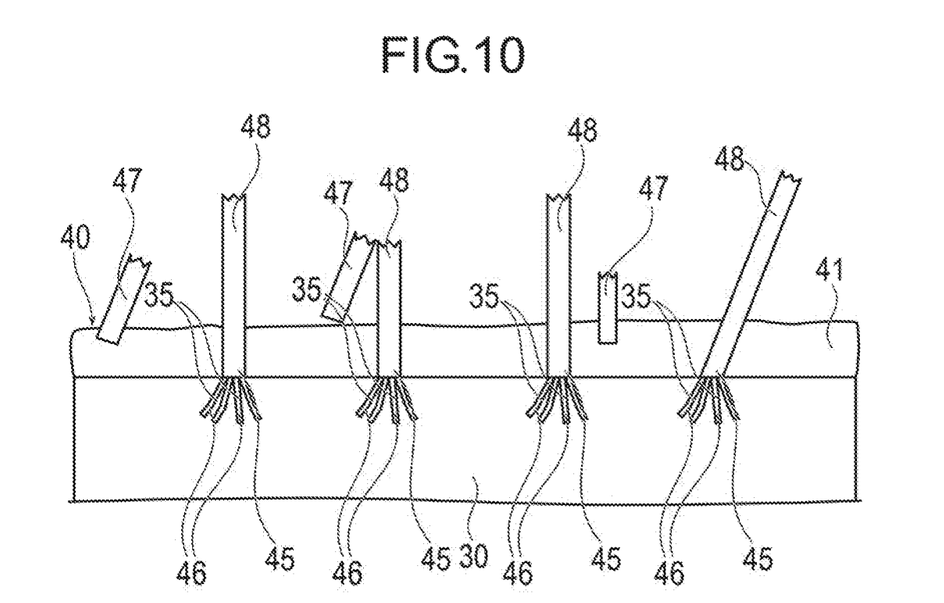
FIG. 10 is a schematic view showing fixed-side elongate bodies and separate-side elongate bodies, as well as a base layer, on the outer surface of a balloon.

As illustrated in FIG. 10, the crystals may include fixed-side elongate bodies 48 (balloon substrate contacting crystal particles) that originally project from the outer surface of the balloon 30 and separate-side elongate bodies 47 (balloon substrate non-contacting crystal particles or crystal particles that do not directly contact the outer surface of the balloon 35) that are separate from the fixed-side elongate bodies 48. The amount of the fixed-side elongate bodies 48 is greater than the amount of the separate-side elongate bodies 47. The separate-side elongate bodies 47 are formed by being separated from the fixed-side elongate bodies 48 upon breaking of the elongate crystals when the balloon 30 is folded in the manner of being wrapped around the inner tube 22. Of the separate-side elongate body 47, at least part of a distal portion, a proximal portion, and a portion between the distal portion and the proximal portion is in contact with the base layer 41. Part of the separate-side elongate body 47 may be embedded in the base layer 41. The presence of the base layer 41 ensures that the fixed-side elongate bodies 48 and the separate-side elongate bodies 47 are prevented from easily falling off (i.e., being removed from) the outer surface of the balloon 30 during transportation by interactions with the base layer 41. The fixed-side elongate bodies 48 and the separate-side elongate bodies 47 are easily released through dissolution of the base layer 41 when the balloon 30 is inflated and the base layer 41 comes into contact with water (blood). The fixed-side elongate bodies 48 and the separate-side elongate bodies 47, which differ in form from one another, are also different in releasing properties. This difference in releasing properties (releasability) is preferable from the viewpoint of action on the living body. The fixed-side elongate bodies 48 may be formed by breaking the crystal or may be formed without breaking the crystal. The base layer 41 may have both the fixed-side elongate bodies 48 that are formed by breaking the crystal and the fixed-side elongate bodies 48 that are formed without breaking the crystal. The fixed-side elongate bodies 48 may be standing (extending or protruding) from the base layer 41 (i.e., distally beyond the base layer 41 towards the surrounding environment) or may be lying along the base layer 41. The base layer 41 may have both the fixed-side elongate bodies 48 that are standing from the base layer 41 and the fixed-side elongate bodies 48 that are lying along the base layer 41.

The length of the crystals fixed to the base layer 41, before breaking of crystal, is, for example, 5 to 20 μm. The length after breaking the crystal is, for example, 3 to 20 μm. The length of the fixed side elongate bodies 48 formed through breaking of crystal is, for example, 5 to 20 μm. The length of the separate-side elongate bodies 47 is, for example, 3 to 10 μm.

Note that the present application is based on Japanese Patent Application No. 2016-058042 filed on Mar. 23, 2016, the contents of which are incorporated herein by reference in entirety thereof.

The detailed description above describes a balloon catheter, balloon catheter manufacturing method and treatment method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon catheter comprising:
an elongated main body extending in an axial direction, the elongated main body possessing a distal portion;
a balloon connected to the distal portion of the elongated main body, the balloon possessing an outer surface, the balloon comprising an interior and being inflatable and deflatable;
a plurality of elongate bodies extending radially away from the outer surface of the balloon, the elongate bodies being crystals of a water-insoluble drug, each elongate body of the plurality of elongate bodies possessing an independent longitudinal axis, a distal end and a proximal end, and a base portion at the proximal end of each elongate body; and
a plurality of elongate body proximal portions extending radially inwardly from the base portion of each elongate body toward the interior of the balloon, the plurality of elongate body proximal portions being continuous extensions of the crystal of the water-insoluble drug extending radially inwardly from the base portion of the elongate body and forming different angles relative to the longitudinal axis of the elongate body,
wherein the plurality of elongate bodies, including their respective base portions, are independent separable non-aggregated bodies,
wherein the balloon is a thin film comprising a plurality of holes in the outer surface of the balloon which do not penetrate fully through the thin film to communicate with the interior of the balloon, the plurality of holes being spaced apart from one another and forming different angles relative to the outer surface of the balloon,
wherein each elongate body proximal portion of the plurality of elongate body proximal portions extends into one hole of the plurality of holes in the outer surface of the balloon toward the interior of the balloon, and has an elongate shape corresponding to an elongate shape of the one hole,
wherein, at the outer surface, there are no extending proximal portions of bodies being crystals of a water-insoluble drug that do not extend into one hole of the plurality of holes.

2. The balloon catheter according to claim 1, wherein each elongate body of the plurality of elongate bodies possess a distal portion and at least the distal portion of each elongate body being hollow.

3. The balloon catheter according to claim 1, wherein each elongate body of the plurality of elongate bodies possess a polygonal cross-section orthogonal to the longitudinal axis of the elongate body.

4. The balloon catheter according to claim 1, wherein each elongate body proximal portion of the elongate body proximal portions possess a maximum width of 5 µm or less.

5. The balloon catheter according to claim 1, wherein the water-insoluble drug is rapamycin, paclitaxel, docetaxel, or everolimus.

6. The balloon catheter according to claim 1, wherein each elongate body proximal portion of the plurality of elongate body proximal portions extends between 0.1 µm and 10 µm towards the interior of the balloon.

7. The balloon catheter according to claim 1, wherein the holes in the outer surface of the balloon each possess a maximum width of 5 µm or less.

8. A method of coating a balloon catheter comprising:
positioning a balloon catheter to apply a coating solution on an outer surface of a balloon of the balloon catheter, the balloon catheter comprising an elongated tubular body which possesses a distal portion, the balloon being attached to the distal portion of the elongated tubular body, the balloon being a thin film that possesses a plurality of spaced apart holes, the holes extending into the outer surface of the balloon, forming different angles relative to the outer surface of the balloon, and not fully penetrating through the thin film to communicate with an interior of the balloon;
applying the coating solution to the outer surface of the balloon of the balloon catheter, the coating solution containing a water-insoluble drug, an organic solvent and water;
volatilizing the organic solvent to cause growth of crystals of the water-insoluble drug that extend from the outer surface of the balloon, each of the crystals of the water-insoluble drug extending from the outer surface of the balloon forming an elongate body, each elongate body possessing a base portion; and
the volatilizing of the organic solvent causing growth of the crystals of the water-insoluble drug into the holes on the outer surface of the balloon to form a plurality of elongate body proximal portions on each elongate body, each elongate body proximal portion of the plurality of elongate body proximal portions on each elongate body continuously extending from the base portion of each elongate body into one hole of the plurality of holes in the outer surface of the balloon toward the interior of the balloon, and having an elongate shape corresponding to the elongate shape of the one hole, the plurality of elongate body proximal portions forming different angles relative to the longitudinal axis of the elongate body, and the plurality of elongate bodies, including their respective base portions, being independent separable non-aggregated bodies,
wherein, at the outer surface, there are no extending proximal portions of bodies being crystals of a water-insoluble drug that do not extend into one hole of the plurality of holes.

9. The method according to claim 8, wherein the holes in the outer surface of the balloon each possess a maximum width of 5 µm or less.

10. The method according to claim 8, wherein the coating solution is applied through a dispensing tube while the dispensing tube is in contact with the outer surface of the balloon.

11. The method according to claim 10, further comprising giving a physical stimulus to the coating solution to cause formation of crystal nuclei of the water-insoluble drug.

12. The method according to claim 11, wherein the physical stimulus includes rotating the balloon catheter relative to the dispensing tube.

13. The method according to claim 8, further comprising forming the holes in the outer surface of balloon.

14. The method according to claim 8, further comprising folding the balloon to break a distal portion of at least some of the elongate bodies after the volatilizing of the organic solvent.

15. A treatment method for delivering a drug to a lesion affected area in a body lumen in a living body, the treatment method comprising:
introducing a balloon catheter into the living body, the balloon catheter comprising an elongated tubular body, a balloon attached to a distal portion of the elongated tubular body, and a plurality of elongate bodies extending radially outward from the outer surface of the balloon catheter, the elongate bodies being crystals of a water-insoluble drug, each elongate body of the plurality of elongate bodies possessing a base portion and a plurality of elongate body proximal portions continuously extending from the base portion of each elongate body toward an interior of the balloon and forming different angles relative to the longitudinal axis of the elongate body, and the plurality of elongate bodies, including their respective base portions, being independent separable non-aggregated bodies;
moving the balloon catheter within the living body into the body lumen to position the balloon of the balloon catheter at the lesion affected area;
inflating the balloon to outwardly expand the balloon toward the living body tissue in the lesion affected area, the inflating of the balloon causing at least some elongate bodies of the plurality of elongate bodies to contact the living body tissue in the lesion affected area and to be released from the outer surface of the balloon; and
deflating the balloon after causing the at least some elongate bodies of the plurality of elongate bodies to contact the living body tissue in the lesion affected area and to be released from the outer surface of the balloon, and withdrawing the balloon out of the body lumen after deflating the balloon,
wherein the balloon is a thin film comprising a plurality of holes in the outer surface of the balloon which do not penetrate fully through the thin film to communicate with the interior of the balloon, the plurality of holes being spaced apart from one another and forming different angles relative to the outer surface of the balloon,
wherein each elongate body proximal portion of the plurality of elongate body proximal portions extends into one hole of the plurality of holes in the outer surface of the balloon towards the interior of the balloon, and has an elongate shape corresponding to an elongate shape of the one hole,
wherein, at the outer surface, there are no extending proximal portions of bodies being crystals of a water-insoluble drug that do not extend into one hole of the plurality of holes.

16. The treatment method according to claim 15, wherein the releasing of the at least some of the plurality of elongate bodies from the outer surface comprises releasing adjacent elongate bodies together.

17. The treatment method according to claim 16, wherein when the adjacent elongate bodies are released together, the elongate body proximal portions of one of the adjacent elongate bodies entangle with the elongate body proximal portions of an other of the adjacent elongate bodies.

18. The treatment method according to claim 15, wherein the water-insoluble drug is rapamycin, paclitaxel, docetaxel, or everolimus.

19. The treatment method according to claim 15, wherein the holes in the outer surface of the balloon each possess a maximum width of 5 μm or less.

* * * * *